United States Patent [19]
Tschopp

[11] 3,943,185
[45] Mar. 9, 1976

[54] DIOLEFIN PRODUCTION AND PURIFICATION

[75] Inventor: Lloyd D. Tschopp, Humble, Tex.

[73] Assignee: Petro-Tex Chemical Corporation, Houston, Tex.

[22] Filed: May 28, 1974

[21] Appl. No.: 473,341

[52] U.S. Cl. .................. 260/680 E; 260/681.5 R
[51] Int. Cl.² ................ C07C 5/48; C07C 7/02
[58] Field of Search ............ 260/680 E, 681.5 R

[56] References Cited
UNITED STATES PATENTS

| | | | |
|---|---|---|---|
| 2,414,651 | 1/1947 | Latchum | 260/681.5 R |
| 3,402,215 | 9/1968 | Woerner et al. | 260/680 R |
| 3,412,171 | 11/1968 | Welch et al. | 260/680 E |
| 3,474,155 | 10/1969 | Tschopp et al. | 260/680 E |

Primary Examiner—Paul M. Coughlan, Jr.
Attorney, Agent, or Firm—N. Elton Dry; Kenneth H. Johnson

[57] ABSTRACT

A process for producing a stream of oxidatively dehydrogenated $C_4$ hydrocarbons with substantially all of the oxygen and inert noncondensable gases removed comprising absorbing the $C_4$ hydrocarbons in an absorber oil in a first zone; stripping oxygen and inert noncondensable gases from the mixture of adsorber oil and $C_4$ hydrocarbons in a second zone which is operated under conditions of temperature and pressure to maintain an aqueous phase in the second zone; and withdrawing (1) a predominately aqueous phase from the second zone, (2) an overhead of predominately all of the oxygen and inert noncondensable gases and a bottoms of adsorber oil and $C_4$ hydrocarbon substantially free of oxygen and inert noncondensable gases.

9 Claims, 2 Drawing Figures

DIOLEFIN PRODUCTION AND PURIFICATION

BACKGROUND OF THE INVENTION

This invention relates to a process for the purification of unsaturated hydrocarbons from a gaseous mixture containing hydrocarbons and relatively noncondensable gases including oxygen and $CO_2$.

Unsaturated hydrocarbons such as styrene, butene and butadiene are commercially produced by the catalytic dehydrogenation of more saturated hydrocarbons. Butadiene is produced in large quantities by the dehydrogenation of butane and butene. Improved processes for the preparation of unsaturated hydrocarbons such as butenes, butadiene-1, 3, isoprene or styrene are processes wherein hydrocarbons such as butane, butene, isopentene, isopentane or ethylbenzene are dehydrogenated at elevated temperatures in the presence of catalysts and oxygen (halogen may also be present). Superior results and yields of products are thereby obtained. However, the product streams contain not only the desired unsaturated hydrocarbons but also may contain various by-products such as CO, $CO_2$, hydrogen, nitrogen, oxygen, oxygenated hydrocarbons, acetylenic compounds, unreacted hydrocarbon, etc. When air is used as a source of oxygen, the effluent from the dehydrogenation reactor will contain large quantities of certain relatively noncondensable gases, such as nitrogen. The gaseous effluent will also contain varying amounts of steam.

Various problems exist in regard to the economic separation and purification of unsaturated hydrocarbons produced by oxidative dehydrogenation which are not encountered in the recovery of products produced by dehydrogenation in the absence of oxygen. Consequently, techniques utilized for the recovery and purification of products derived from the dehydrogenations in the absence of oxygen have not generally been found satisfactory for the recovery of effluents resulting from oxidative dehydrogenation reactions. The presence of large quantities of oxygen, by-products gases, and gases such as nitrogen create entirely different problems from those previously encountered. Furthermore, another problem encountered in the recovery of effluents from oxidative dehydrogenation reactors is that a high degree of fouling of recovery equipment is encountered. In view of these and other problems, a process was needed which would recover and purify the unsaturated hydrocarbon in an economical and efficient manner.

In U.S. Pat. Nos. 3,402,215 and 3,412,171, a process was disclosed whereby the unsaturated product may be recovered from the various gases present and from the acetylenic compounds at the same time. According to those processes, a particular gaseous mixture comprising unsaturated hydrocarbons, oxygen and inert noncondensable gases may be separated by intimately contacting the gaseous mixture in an absorbing zone with an oil having a boiling point or a boiling point range from about 170° to 320° F (at least 95 volume percent of the oil boils within this range). Acetylenic compounds were an impurity to which particular attention was given in these processes.

The absorbing oil, containing absorbed gases, including dehydrogenated material, unreacted feed, oxygen, inert noncondensable gases and steam or entrained water is cooled and is passed to separating zone where the predominate amount of oxygen and inert noncondensable gases and some acetylenic compounds are removed. In the present invention, this particular zone is not intended to achieve a separation of acetylenic compounds and their removal at this point is at most incidental to the removal of oxygen and inert noncondensable gases (CO, $CO_2$ and nitrogen are considered to be the principal constituents of the inert noncondensable gases when air is fed to the oxidative dehydrogenation zone).

The optimal operation of the separating zone should achieve total removal of oxygen and the inert noncondensable gases without loss of the product unsaturated hydrocarbons or unreacted starting materials, e.g., butadiene and n-butene, respectively. In practice, of course, the separation is less than optimal, in that product unsaturated hydrocarbon and other desirable hydrocarbons are carried overhead with the stripped oxygen and inert noncondensable gases. The practice in the past, in the operation of the separator has been to carry some steam and entrained water overhead with the oxygen and inerts with the major portion passing out with the bottoms. The next step in the process is the removal of the hydrocarbons from the absorber oil. The hydrocarbons then go on to a final finishing operation and the lean oil is preferably recycled to the absorbing zone.

Conditions which allowed the water to be removed with the bottoms also resulted in less than the best separation of oxygen and $CO_2$ from hydrocarbon product. This invention provides a more economical process, both in terms of cost and hydrocarbon product, since less hydrocarbon product passes overhead in the oxygen inert gas stream and better separation of oxygen and inert noncondensable gases from hydrocarbon product are achieved. Another benefit of the present invention is the substantial removal of water from the hydrocarbon product stream.

The present invention has as its goal the disclosure of a process which will provide an improved separation of hydrocarbon product from the oxygen and inert noncondensable gases overhead in a stripping zone and recovery of a liquid stream of water and a purer hydrocarbon product.

SUMMARY OF THE INVENTION

The present invention is an improvement in the process of separating olefincally unsaturated hydrocarbons, oxygen and inert noncondensable gases comprising contacting the gaseous mixture in a first zone with an oil having a boiling point of a boiling point range from about 170° to 320° F. The substantial portion of the oil will have boiling points within these ranges, i.e., 95 volume percent, although small quantities may be outside thereof.

The first zone is maintained at a temperature of between 55° and 150° F. and a pressure between 100 p.s.i.g. and 200 p.s.i.g. From the first zone a liquid composition containing the oil and gases absorbed therein is taken off and preferably cooled in a second zone to a temperature of no greater than 100° F. The cooled product from the second zone is then transferred to a third zone. In the third zone a gaseous mixture comprising oxygen and inert noncondensable gases is taken off. Also from the third zone a predominately organic liquid composition comprising the oil containing the unsaturated hydrocarbons dissolved therein is taken off. The improvement comprises operating the third zone at a temperature between 55° and 190° F and a pressure between —5 p.s.i.g. and 70 p.s.i.g. to produce liquid aqueous phase in said zone and removing a liquid stream which can be characterized as being predominately aqueous. The organic liquid composition from the third zone may then be separated in a fourth zone, such as by stripping, to recover the unsaturated hydrocarbons. Similarly, the aqueous liquid phase may be further separated to completely remove any entrained organic liquids.

The conditions of operating the third zone or oxygen stripper encompass substantially the same range of temperature and pressure as the prior art, however, it has been discovered that by selecting the appropriate combination of conditions the substantial improvements in separating and removing oxygen, the inert noncondensable gases and water from the hydrocarbon product can be obtained. The conditions for operation within the given ranges are those which cause an accumulation of a water phase in the zone, i.e., a flooding condition.

The pressure-temperature conditions of the present invention can be seen by reference to FIG. 2 which plots the feed temperature to the top tray versus pressure. For any given temperature on line $x-y_1$ the minimum pressure in the separator required to obtain the improved separations is given on the y axis. Thus, line $x-y_1$ represents the lower limit of the relationship between temperature and pressure. In order to achieve more than a minimal improvement according to the present invention higher pressures up to and including those shown in relation to line $x-y_2$ are preferred for a given temperature. The upper pressure limitation is about 70 p.s.i.g., since at pressures higher than this bottoms temperature would be high enough to cause fouling in the tower and reboiler. Pressures higher than those corresponding to a given temperature than on line $x-y_2$ are permissable (as indicated above) but not necessary to achieve superior separations.

DETAILED DESCRIPTION OF THE INVENTION AND PREFERRED EMBODIMENTS

Figure 1:
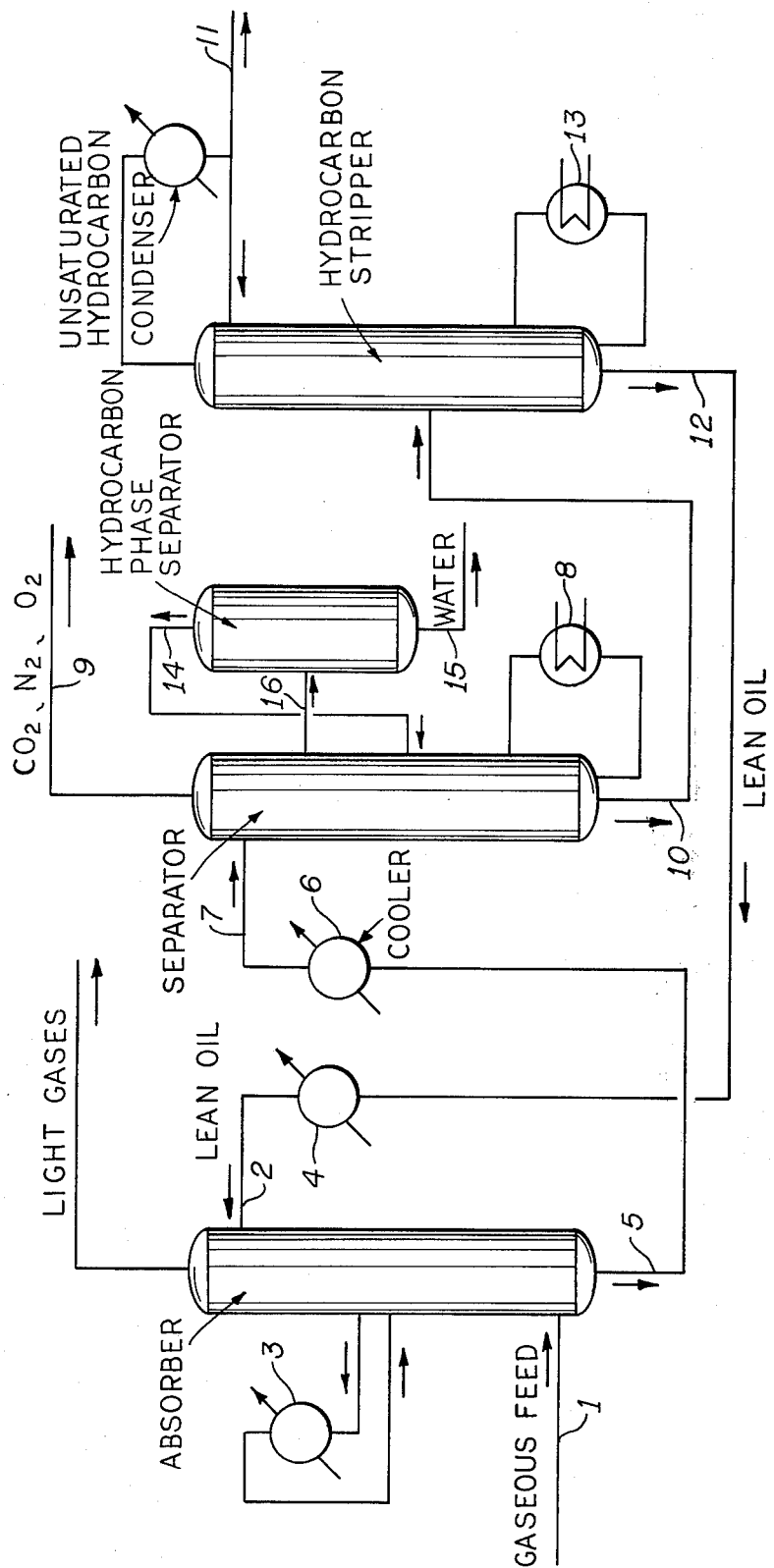

The first zone, wherein the gaseous mixture is contacted with the oil may be any suitable equipment for absorbing the gaseous mixture in the oil. This absorber may be e.g., a column having bubble cap trays or perforated plates or may be a packed column or the like. The second and third zones, wherein the gaseous material is taken off overhead, may be any suitable equipment to perform this function. One method for stripping off these gases is to feed the composition to the top or near the top of a fractionating column such as a tray type or packed column. Although less preferred, it is also possible to flash off the gases in the second zone in equipment so designed. Preferred equipment for the zones are plate columns (perforated, valve, bubble cap, etc.) and packed columns. Also it is preferred to feed the composition to the top one-third of the second and third zone columns respectively. The gaseous mixture to be treated containing the unsaturated hydrocarbon, noncondensable gases, oxygen, by-product actylenes and various other by-products may be obtained from a variety of sources. However, the invention is particularly suitable for the purification of gaseous effluents resulting from the oxidative dehydrogenation of hydrocarbons utilizing air or oxygen diluted with noncondensable diluents such as nitrogen or helium. Halogens may be added to increase the yields and selectivities of the desired product. Examples of processes for dehydrogenation in the presence of oxygen are found in U.S. Pat. Nos. 3,207,805 through 3,207,811; 3,159,688; 3,205,280; 3,080,435; 3,284,536; 3,270,080; 3,303,235 through 3,303,238 and 3,526,675.

Hydrocarbons to be oxidatively dehydrogenated are acyclic, cycloaliphatic or alkyl aryl hydrocarbons of 3 to 9 carbon atoms, having at least one

grouping. The dehydrogenation will produce compounds having double and/or tripple bonds. Thus, butadiene-1,3 and/or vinylacetylene may be produced from any of the methyl butenes, such as 2-methyl butene-2 or 3-methyl butene-1 or mixtures thereof. Isoprene may also be produced from methyl butanes, such as 2-methyl butane; also olefins and diolefins may be produced from saturated hydrocarbons, for example, vinyl acetylene, butadiene and butene may be produced from n-butane. A mixture of monoolefins and diolefins may also be produced, such as a mixture of butadiene-1,3 and butenes from a feedstock of a mixture of n-butane and butene. Cyclohexane may be dehydrogenated to cyclohexene and/or benzene. Ethyl benzene or ethylcyclohexane may be dehydrogenated to styrene. Good results have been obtained with a feed containing at least 50, and preferably at least 75, mol percent of an acyclic aliphatic hydrocarbon, such as the hydrocarbons of 4 to 5 carbon atoms having a straight chain of at least four carbon atoms and single double bond; preferred are the monoethylenically unsaturated compounds or mixtures of saturated and unsaturated compounds.

Oxygen will generally be supplied to the dehydrogenation zone in the range of about 0.20 mols of oxygen to 2.0 or 3.0 mols of oxygen per mol of hydrocarbon to be dehydrogenated. A preferred range for the oxygen is from about 0.3 to 1.50 mols of oxygen per mol of hydrocarbon to be dehydrogenated. Either air or oxygen diluted with diluent such as nitrogen, helium and the like may be utilized. Steam may be fed to the dehydrogenation zone in amounts such as from about 2 to 40 mols of steam per mol of hydrocarbon to be dehydrogenated. An advantageous range is from 2 to 20 mols of steam per mols of hydrocarbon. When halogen is employed the halogen will suitably be present in an amount of from 0.001 to 0.1 mol per mol of hydrocarbon fed.

The oxidative dehydrogenation reaction may be conducted in the absence of contact catalysts, but better results are obtained if the reaction is conducted in the presence of metal or metal compound catalysts. The oxidative dehydrogenation reactor may be a fixed or fluid bed reactor. Reactors such as those conventionally used for the dehydrogenation of hydrocarbons to butadiene may be employed. The total pressure in the dehydrogenation zone may suitably be about atmospheric pressure. However, higher pressures or vacuum may be used. Pressures such as from about atmospheric (or below) up to about 100 to 200 p.s.i.g. may be employed. The oxidative dehydrogenation reaction will normally be conducted at a temperature of reaction between about 600° F. to about 1,500° F. or higher, although generally the maximum temperature in the reactor will be within the range of about 700° and 1,300° F. This temperature of the reaction is measured at the maximum temperature in the reactor. The flow rates of the reactants may be varied quite widely and will be dependent somewhat on whether fixed or fluid bed reactor is employed. Good results have been obtained with flow rates of the hydrocarbon to be oxidatively dehydrogenated ranging from about ¼th to 25 liquid volumes of hydrocarbon to be dehydrogenated per volume of reactor zone per hour, with the volumes of hydrocarbon being calculated as the equivalent amount of liquid hydrocarbons at standard conditions of 15.6° C and 760 millimeters of mercury absolute. For the purpose of calculating flow rates the reaction zone is defined as the portion of the reactor which contains catalyst and which is at a temperature of at least 600° F. In other words, the volume of the reaction zone is equivalent to the volume of the catalyst zone if it were empty. The residence or contact time of the reactants in the oxidative dehydrogenation zone depends on several factors involved in the reaction. Contact times such as about 0.001 to about 5, 10 or 25 seconds have been found to give excellent results. Under certain conditions, higher contact times may be utilized. Contact time is the calculated dwell time of the reaction mixture in the reaction zone assuming the mols of product mixture are equivalent to the mols of feed.

The effluent from the oxidative dehydrogenation zone will contain the impure unsaturated hydrocarbon products, oxygen, various impurities including oxygenated hydrocarbons, noncondensable inert gases and depending upon the particular process perhaps some unconverted feed of halogenated compounds. The dehydrogenated product corresponds to the feed to the oxidative dehydrogenation zone but will have a portion thereof at a higher degree of unsaturation. If air was used as the source of oxygen, nitrogen will be present in relatively large quantities as a noncondensable gas. Steam may be present in an amount up to 96 mol percent of the total effluent, such as from about 5 to 96 mol percent. The organic phase including dehydrogenated product, any unreacted feed, acetylenic compounds, oxygenated hydrocarbons, polymer and tar and precursors thereof and any organic decomposition products usually ranged from about 3 to 50 mol percent of the effluent and generally will be within the range of about 3 to 30 or 35 mol percent of the effluent. The noncondensable gases (under the conditions encountered), such as nitrogen, will be present in an amount of from or about 20 to 93 mol percent of the total effluent.

The effluent gases leaving the oxidative dehydrogenation zone will generally be at a temperature of about or greater than 600° F. or 700° F. to 1,600° F depending upon the particular process conditions. The effluent gases are then cooled prior to further treatment according to this invention. The reactor effluent may be cooled by any means or combination of means as by quenching followed by employing waste heat boilers, condensers, vapor separators and the like. Ordinarily, water will be removed as condensed steam from the gaseous effluent during this cooling operation. This cooled gaseous stream may then be treated according to the present invention or may first be processed to remove carbonyl compounds or halogenated compounds such as the process of U.S. Pat. No. 3,200,166.

A preferred embodiment of the invention is illustrated in the drawing. The gas feed 1 may be obtained from any suitable source, such as from the dehydrogenation of hydrocarbons in the presence of oxygen to form a mixture of inert noncondensable gases, unsaturated hydrocarbons, unreacted hydrocarbons, oxygenated hydrocarbons, methyl acetylene, oxygen, nitrogen, water and various other by-products, such as $CO_2$ and CO. The oxidative dehydrogenation reactor effluent generally will be cooled such as by quenching and by indirect heat exchange prior to entering the absorber. Also, some of the steam may be removed by means such as knockout vessels and the like. The gaseous feed 1 will comprise or consist, exclusive of any water present, from 3.5 to 80 mol percent unsaturated hydrocarbon, from .001 to 3 mol percent oxygen, from 20 to 93 mol percent inert non-condensable gases (this term refers to non-hydrocarbons such as $H_2$, $N_2$, $CO_2$, CO, helium, and the like which are not condensable under the condition of reaction). A preferred range of inert noncondensable gases is from 45 to 89 mol percent with a particularly preferred range of 40 to 75 mol percent inert noncondensable gases. The gaseous feed 1 will also contain from 0.003 to 15 mols of water, either as steam or as entrained water, per mol of total hydrocarbon. Based on the total organic content of the gaseous feed 1, the total hydrocarbons will constitute at least 85 mol percent of the organic portion of this gaseous feed 1. Preferably, the composition of the gaseous feed 1, exclusive of any water present, will be from 5 to 65 mol percent unsaturated hydrocarbons, from .001 to 1.0 (preferably less than 0.3) mol percent oxygen, from 45 to 89 mol percent inert noncondensable gases, and the total hydrocarbons will constitute at least 95 mol percent of the organic portion of the gaseous feed 1. Also, preferably, water will be present as steam in an amount of from 0.003 to 10 mols of steam per mol of total hydrocarbon in the gaseous feed.

Lean oil 2 will preferably be fed to the top of the absorber in order to have countercurrent contact with the gaseous feed 1 which is rising in the tower. According to this invention, the lean oil must be of a particular composition. The oil must have a boiling point at standard atmospheric pressure of from or about 170° to 320° F. and preferably from or about 175° F. to 280° F. The lean oil will predominantly be made up of compounds having elements selected from the group consisting of carbon, hydrogen, oxygen, nitrogen, halogen, and mixtures thereof and will preferably consist essentially of these elements. Of course, the lean oil may contain impurities, particularly preferred as lean oils are hydrocarbons within the stated boiling ranges which have the formula $C_xH_y$, wherein $x$ is a number from 6 to 9 inclusive and $y$ is a number from 6 to 18 inclusive; suitable compounds to be used as lean oils are methylcyclohexane, 2,4,4-trimethyl-1-pentene, 3,4,4-trimethyl-1-pentene, 2,4,4-trimethyl-2-pentene, 3,3,4-trimethyl-1-pentene, 2,3,4-trimethyl-1-pentene, 2,3,3-trimethyl-1-pentene, 2,5-dimethylhexane, 2,4-dimethylhexane, 2,2,3-trimethylpentane, benzene, toluene, 3,4,4-trimethyl-2-pentene, 2,3,4-trimethylpentane, 2,3,3-trimethylpentane, 2,3,4-trimethyl-2-pentene, butadiene dimer (particularly vinyl cyclohexene), diisobutylene, paraffins containing 8 carbon atoms, such as those obtained from an alkylation plant, amylamine, 3-chloro-pentane, n-butylamine, m-dioxane, nitro-ethane, mixtures thereof, and the like. In some instances, mixtures of the various compounds may be blended to produce desirable lean oils; for example, it has been discovered that a combination of one or more compounds having a relatively high boiling point together with one or more compounds having a relatively low boiling point can result in excellent lean oils.

The absorber is operated within a temperature of from 60° to 150° F. and, more desirably, within the range of 80° to 135° F. The pressure in the absorber will be from 100 p.s.i.g. to 200 p.s.i.g. and, more desirably, from 120 p.s.i.g. to 140 p.s.i.g. According to this preferred embodiment, the absorber does not contain a reboiler. That is, the absorber is not a fractionating absorber.

During operation of the process, some impurities will be encountered in the recycling lean oil. Nevertheless, the lean oil 2 entering the top of the absorber should have a composition containing predominately, and preferably at least 65 mol percent of, the compounds in the described class. If relatively large amounts of higher boiling compounds, such as the xylenes, are present, we have discovered that there is considerable polymer formation and its attendent equipment fouling. Means may be provided to purify the lean oil to remove heavier materials, such as by distillation, prior to recirculating the lean oil to the absorber.

Suitably, coolers such as 3 and 4 may be inserted into the absorber system in order to maintain the required reaction conditions in the absorber. Also, not shown, the absorber may have incorporated a sponge oil unit to recover lean oil going overhead from the absorber. This lean oil coming overhead may be purified, such as by absorption and stripping in the sponge oil unit and returned to the lean oil system at any point.

The liquid composition 5 leaving the absorber comprises the fat oil containing absorbed gases. This composition may then be cooled in cooler 6. Any suitable means for cooling this composition may be utilized, such as a heat exchanger cooled by refrigerant or cooled water.

The cooled composition 7 is then fed to the separator. The composition 7 must be fed to the top two-thirds of the separator, preferably the composition 7 is fed to the upper one-third of the separator, and, usually is fed to the top tray of the separator. Heat is added to the separator, such as by a reboiler 8. In the separator, oxygen, together with large quantities of inert noncondensable gases including nitrogen, $CO_2$, and various $C_2$'s and $C_3$'s, are taken off overhead. Exclusive of any water present, in the separator, preferably at least 1 mol percent of the stream 7 is removed as an overhead gaseous composition 9. The gaseous overhead 9 from the separator may then be disposed of in any environmentally safe manner. The gaseous composition 9 may be returned to the inlet for the compressors compressing the reactor effluent or may be fed to separate compressors and thereafter may be recycled to the gaseous feed 1 entering the absorber. The gaseous overhead 9 may also be cooled and collected in an accumulator (not shown) from which the condensed portion is recycled to the separator and the gaseous uncondensed overhead from the accumulator may then be sent to a compressor and thereafter fed to the gaseous feed line 1 or utilized otherwise. The water, which in the prior manner of operation was substantially allowed to pass out with the bottoms is now retained in the separator and a liquid aqueous phase is removed from generally the middle one-third of the separator. This method allows for a phase separation within the separation zone, however, a slight different manner of operation provides for overdrawing the aqueous phase, i.e., taking some organic liquid phase, in order to insure that all of the water is being removed at this point.

FIG. 1 shows an external phase separator and allows the overdraw. The organic, i.e., hydrocarbon phase can be returned to the separator at a point below the aqueous draw or it can be recycled to the absorber (not shown) or otherwise treated depending on its characterization at any particular time. The water phase 15 may be recycled to the steam generators, biologically treated and returned to surface water or otherwise dumped according to permit.

The separator will be operated at a temperature of between about 55° F. and 190° F and a pressure of between about −5 p.s.i.g. and 70 p.s.i.g., with the preferred temperature range being from 70° to 160° F. and the preferred pressure range being between 15 p.s.i.g. and 50 p.s.i.g. within the limits noted above.

It is proposed that the improved separation of hydrocarbon from the overhead gases in the separator may be achieved by an internal reflux within the separator as a result of the increased pressure, however, the present invention does not rely on any mechanism as its basis and is not limited thereby. If the mechanism is as speculated, then supposedly this same reflux could be carried out outside of the separator, that however, could be a very dangerous operation, since oxygen is present in the overhead and the concentration of a product such as butadiene and oxygen in an external reflux could lead to the formation of organic hydroperoxides, which are unstable, and the polymerization of the olefinic material.

The mixed hydrocarbon-aqueous liquid phase stream 16 may be taken off in the middle 80% of the separator, but is generally taken off in the middle third of the separator. For example, in a 28 tray tower, the draw for stream 16 would be from the twelfth to eighteenth tray or more preferably the sixteenth tray or approximately at the middle of the tower.

The liquid composition 10 is fed to the hydrocarbon stripper wherein the unsaturated hydrocarbon is stripped from the lean oil and taken off overhead as 11. The lean oil 12 is taken off from the stripper and may be purified by means not shown prior to returning to the absorber as 2. The hydrocarbon stripper will have means for heating, such as by the reboiler 13. The unsaturated hydrocarbon 11 coming overhead may then be sent for further purification, for example, to separate the unsaturated hydrocarbon from the remaining hydrocarbons.

The invention will be illustrated for the purification of butadiene-1,3. Butadiene is obtained by oxidative dehydrogenation of $C_4$ hydrocarbons. The effluent from the reactor is cooled and partially purified. The resulting gaseous stream is then processed according to this invention, with reference being made to the drawing. The gaseous feed 1 contains 15 mol percent butadiene, 11 mol percent total butene and butane, 0.2 mol percent oxygen, 73.8 mol percent inert noncondensable gases (including $H_2$, $N_2$, $CO_2$, CO and helium). The gaseous feed 1 also contains 0.7 mols of water per 100 mols feed.

Lean oil 2 is fed to the top of the absorber and the gaseous feed 1 is fed to the bottom of the absorber. The lean oil 2 has a boiling point range from about 216° to 293° F. and contains principally 4-vinyl-1-cyclohexene (VCH) and toluene.

The absorber is operated with a bottoms temperature of about 130° F. and an overhead temperature of 84° F. The pressure in the absorber is about 125 p.s.i.g. The absorber does not contain a reboiler. The absorber is equipped with a sponge oil unit to recover lean oil going overhead from the absorber.

The liquid composition 5 leaving the absorber comprises the fat oil containing absorbed gases. This composition is cooled in cooler 6 and is transmitted to the top of the separator. Heat is added to the separator by reboiler 8. The separator is operated at a bottoms temperature of 155.1° F and pressure 43 p.s.i.g., and an overhead temperature of about 93.2° F. and pressure of 40 p.s.i.g. A side draw 16 is at about 120° F. In the separator, oxygen, together with large quantities of inert, noncondensable gases are taken off overhead at 40 p.s.i.g.

A detailed description of the streams into and from the separator is shown in TABLE I.

TABLE I

| STREAM | SEPARATOR OPERATED WITH WATER SIDE DRAW | | | |
|---|---|---|---|---|
|  | 7 | 9 | 10 | 16[2] |
| COMPOSITION | MOL%* | MOL%* | MOL%* | MOL%* |
| Oxygen | 39.8ppm | 0.19 | 0 | 0 |
| Nitrogen | 6898 ppm | 32.81 | 0 | 0 |
| CO | 71.6ppm | 0.34 | 0 | 0 |
| $CO_2$ | 4599 ppm | 21.60 | 28.5ppm | 1.28 |
| n-Butane | 2.29 | 2.33 | 2.29 | 2.57 |
| n-Butenes | 15.37 | 15.11 | 15.37 | 17.22 |
| Butadiene | 25.52 | 26.44 | 25.49 | 28.93 |
| VCH | 20.41 | 0.30 | 20.85 | 18.31 |
| Toluene | 35.24 | 0.88 | 36.00 | 31.69 |
| Ratio Hydrocarbon Streams, Mol/hour | 47.59 | 1.0 | 46.47 | 0.13 |
| Water Gallon/min. | 2.03[1] | 0.14 | Nil | 1.89 |

[1]Saturated water from absorber bottoms and .41 free water.
[2]Two liquid phases.
*Exceptions noted in Table as ppm (parts per million).

The liquid composition 10 is fed to the hydrocarbon stripper wherein unsaturated hydrocarbons are stripped from the lean oil and taken off overhead as 11. The water phase is allowed to separate in the phase separator, and the organic portion returned to the separator via 14. The lean oil 12 is purified by means not shown and returned to the absorber as lean oil 2. The unsaturated hydrocarbon 11 coming overhead from the hydrocarbon stripper is then further purified to produce butadiene-1,3 in a composition of at least 99.1 mol percent purity.

The utilization of process with a gaseous stream 1 wherein the major hydrocarbon component is isoprene instead of butadiene-1,3 gives the advantages of the present invention.

For comparison, a separation on a similar feed 7 was carried out according to the prior art, i.e., without water draw 16. The conditions of operation were separator bottoms 128.5° F., pressure 36 p.s.i.g., and overhead about 89° F., pressure 24 p.s.i.g. The details on the stream compositions is given in Table II. FIG. 1 is used for this example except for stream 16, 14, 15 and the phase separator (the water side draw related components).

TABLE II

| STREAM | SEPARATOR OPERATED WITHOUT WATER SIDE DRAW | | |
|---|---|---|---|
|  | 7 | 9 | 10 |
| COMPOSITION | MOL%* | MOL%* | MOL%* |
| Oxygen | 39.9ppm | 0.16 | 8.1ppm |
| Nitrogen | 6912 ppm | 31.24 | 529 ppm |
| CO | 71.8ppm | 0.31 | 8.1ppm |

TABLE II-continued

| STREAM | SEPARATOR OPERATED WITHOUT WATER SIDE DRAW | | |
|---|---|---|---|
|  | 7 | 9 | 10 |
| $CO_2$ | 4578 ppm | 8.12 | 2978 ppm |
| n-Butane | 2.29 | 3.15 | 2.27 |
| n-Butenes | 15.37 | 20.34 | 15.26 |
| Butadiene | 25.51 | 35.30 | 25.30 |
| VCH | 20.42 | 0.29 | 20.84 |
| Toluene | 35.25 | 1.09 | 35.97 |
| Ratio Hydrocarbon Streams Mol/Hour | 48.87 | 1.0 | 47.87 |
| Water Gallon/Min. | 2.02 | 0.15 | 1.87 |

*Exceptions noted in Table as ppm (parts per million).

The improvement of the present invention over the prior method is apparent, however, particular notice is directed to the improved pressure drop through the column for the invention, i.e., 3 pounds, whereas the prior method had a 12 pound drop, the almost complete removal of oxygen and noncondensable gases by the invention, and the reduction in loss of butadiene in overhead stream 9.

The invention claimed:
1. In a process for the preparation of unsaturated hydrocarbons without the formation of excessive polymer which comprises:
oxidatively dehydrogenating $C_3$ to $C_9$ hydrocarbons having at least one

grouping, to obtain a gaseous mixture comprising 0.003 to 15 mol percent water per mol of total hydrocarbon, an organic phase comprising 3.5 to 8.0 mol percent, exclusive of water, of an unsaturated hydrocarbon corresponding to said $C_3$ to $C_9$ hydrocarbon and having a higher degree of unsaturation thereover, 20 to 93 mol percent inert noncondensable gases and 0.001 to 3 mol percent oxygen, said total hydrocarbons constituting at least 85 mol percent of the organic phase of said gaseous mixture;
intimately contacting said gaseous mixture in a first zone with a hydrocarbon oil having a boiling point within the range of about 170° to 320° F., said first zone being maintained at a temperature of between about 60° and 150° F. and a pressure of between 100 p.s.i.g. and 200 p.s.i.g.;

removing from said first zone a liquid composition containing said oil and absorbed gases including unsaturated hydrocarbons;

feeding said oil and absorbed gases to a second zone;

removing from said second zone a gaseous mixture of oxygen and inert noncondensable gases;

removing from said second zone an organic liquid composition comprising said oil and absorbed unsaturated hydrocarbons;

separating said organic liquid composition from said second zone to recover said hydrocarbons;

wherein the improvement comprises:

maintaining said second zone at a temperature of between 55° and 190° F. and a pressure of between −5 and 70 p.s.i.g., and removing a mixed hydrocarbon-aqueous liquid phase composition which is predominately water on a molar basis, from said second zone at a point intermediate said removal of the gaseous mixture of oxygen and inert noncondensable gases and the oil and absorbed unsaturated hydrocarbons in said second zone, said water not being returned to said second zone.

2. The process according to claim 1 wherein said second zone is maintained at a temperature of between 70° and 160° F. and at a pressure of between 15 p.s.i.g. and 50 p.s.i.g.

Figure 2:
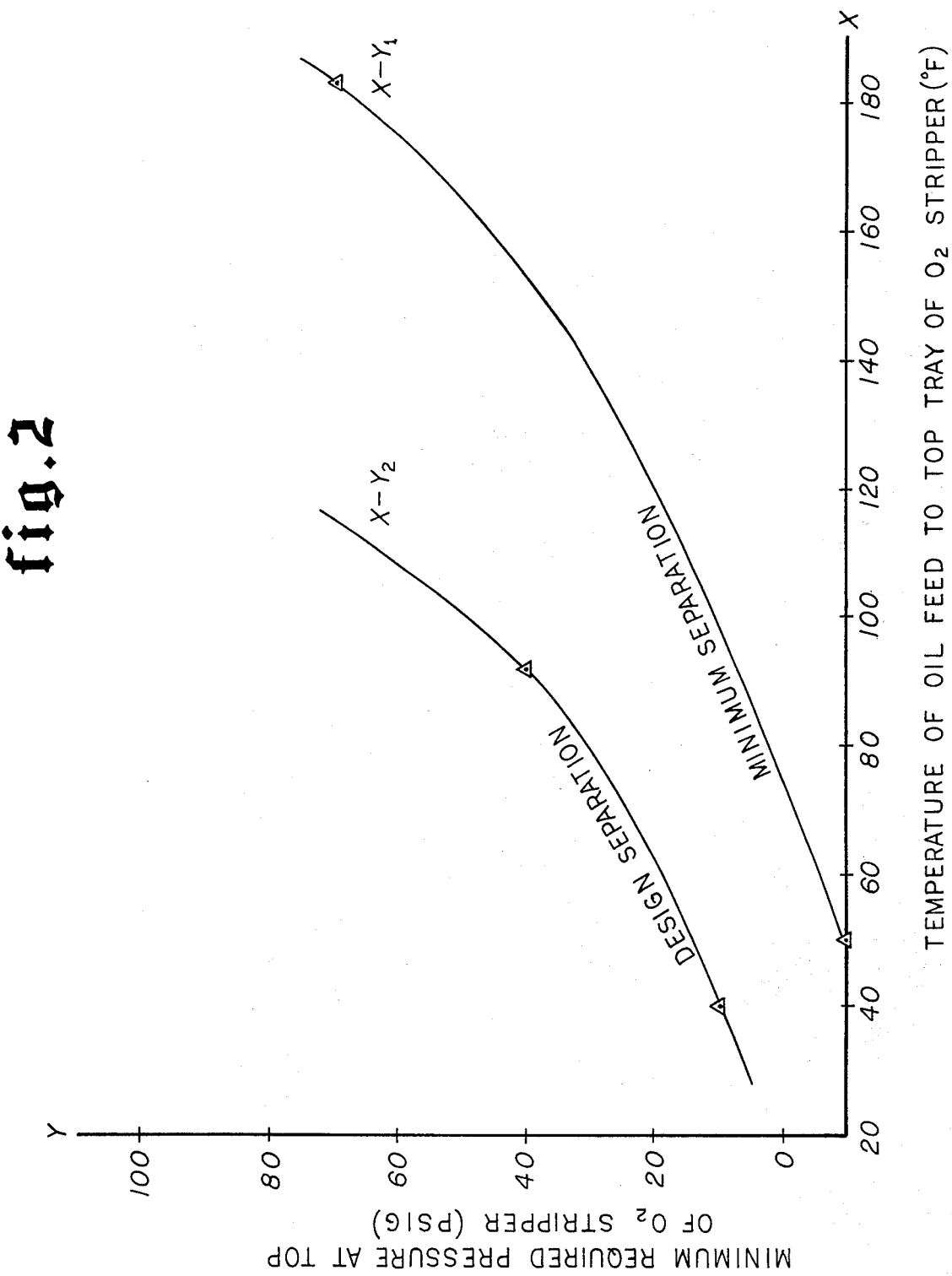

3. The process according to claim 1 wherein the relationship between feed temperature to said second zone and the pressure in said second zone is that shown in the graph of FIG. 2 wherein for any given temperature on line x - $y_1$ the minimum pressure is shown on the y - axis.

4. The process according to claim 1 wherein said hydrocarbon lean oil is recovered and recycled to said first zone.

5. The process according to claim 1 wherein said organic liquid is stripped by heat to remove dissolved hydrocarbons as a volatile fraction and to produce a lean oil containing dissolved therein material heavier than said oil; said oil is purified by distillation to remove said heavier materials therefrom and said purified oil is returned to said first zone as absorber oil.

6. The process according to claim 1 wherein $C_4$ to $C_5$ hydrocarbons are oxidatively dehydrogenated.

7. The process according to claim 6 wherein a normal $C_4$ hydrocarbon is oxidative dehydrogenated.

8. The process according to claim 7 wherein said unsaturated hydrocarbon comprises butadiene -1,3.

9. In a process for preparing unsaturated hydrocarbons without the formation of excessive polymer and having improved recovery of unsaturated hydrocarbons comprising:

oxidatively dehydrogenating normal $C_4$ hydrocarbons having at least one

grouping to obtain a gaseous mixture comprising 0.003 to 15 mol percent water per mol of total hydrocarbon, an organic phase comprising 3.5 to 80 mol percent, exclusive of water, of an unsaturated hydrocarbon, including butadiene-1, 3, 20 to 93 mol percent inert noncondensable gases and 0.001 to 3 mol percent oxygen, said total hydrocarbons constituting at least 85 mol percent of the organic phase of said gaseous mixture;

intimately contacting said gaseous mixture in a first zone with a hydrocarbon oil having a boiling point within the range of about 170° F. to 320° F., said first zone being maintained at a temperature of between about 60° and 150° F. and a pressure of between 100 p.s.i.g. and 200 p.s.i.g.;

removing from said first zone a liquid composition containing said oil and absorbed gases including unsaturated hydrocarbons;

feeding said oil and absorbed gases to a second zone;

removing from said second zone a gaseous mixture of oxygen, inert noncondensable gases and acetylenic compounds;

removing from said second zone an organic liquid composition comprising said oil and absorbed unsaturated hydrocarbons;

separating said organic liquid composition from said second zone to recover said hydrocarbons;

wherein the improvement comprises:

maintaining said second zone at a temperature of between 70° and 160° F and at a pressure between 15 p.s.i.g. and 50 p.s.i.g., accumulating a liquid aqueous phase in said second zone, and removing said liquid aqueous phase therefrom.

* * * * *